United States Patent [19]

Wendelken

[11] Patent Number: 5,445,802
[45] Date of Patent: Aug. 29, 1995

[54] DISINFECTION RACK

[76] Inventor: Martin E. Wendelken, P.O. Box 176, New Milford, N.J. 07407

[21] Appl. No.: 21,048

[22] Filed: Feb. 23, 1993

[51] Int. Cl.⁶ .................. A61L 2/18; A47B 73/00; G03D 5/06
[52] U.S. Cl. .................... 422/302; 422/300; 211/75; 222/187; 239/45; 15/101; 15/104.92
[58] Field of Search ............... 222/187, 151; 239/44, 239/45, 145; 211/75, 120; 422/300, 302; 15/101, 104.92

[56] References Cited

U.S. PATENT DOCUMENTS

| | | | |
|---|---|---|---|
| 1,216,110 | 2/1917 | Goodrow | 211/75 X |
| 1,714,075 | 5/1929 | Carvalho | 15/101 |
| 2,057,946 | 10/1936 | Harris | 211/75 X |
| 2,282,672 | 5/1942 | Nelson | 15/104.92 |
| 2,323,615 | 7/1943 | Martineau | 222/187 X |
| 2,508,945 | 5/1950 | Heuer | 211/75 |
| 4,159,553 | 7/1979 | Graziano | 15/101 |
| 4,325,486 | 4/1982 | Neal | 211/71 |
| 4,482,065 | 11/1984 | Altemose | 211/74 |
| 4,544,529 | 10/1985 | Hoeck | 422/303 |
| 4,687,108 | 8/1987 | Kermodle | 211/13 |
| 4,863,698 | 9/1989 | Ryder et al. | 422/116 |
| 4,887,726 | 12/1989 | Clanire | 211/74 |
| 4,925,630 | 5/1990 | Grunwald | 422/104 |
| 5,106,595 | 4/1992 | Ellenberg | 422/302 |

Primary Examiner—Robert J. Warden
Assistant Examiner—E. Leigh Dawson

[57] ABSTRACT

A disinfection rack to mount, organize, display, and sterilize vials comprising of a reservoir (16) that contains disinfection fluid, which travels along a plurality of wicks (24) into a disinfection chamber (14), where the top of vials (28) remains in contact with the disinfecting fluid. Vials (28) are suspended by the top and neck within said disinfection chamber (14), and is stabilized by a spring (22) also contained within. The disinfection rack can be mounted by attaching a mounting plate (10) to a wall, cabinet, door, or other vertical surface allowing continuous visualization and sterilization of vials while in said disinfection chamber (14).

1 Claim, 3 Drawing Sheets

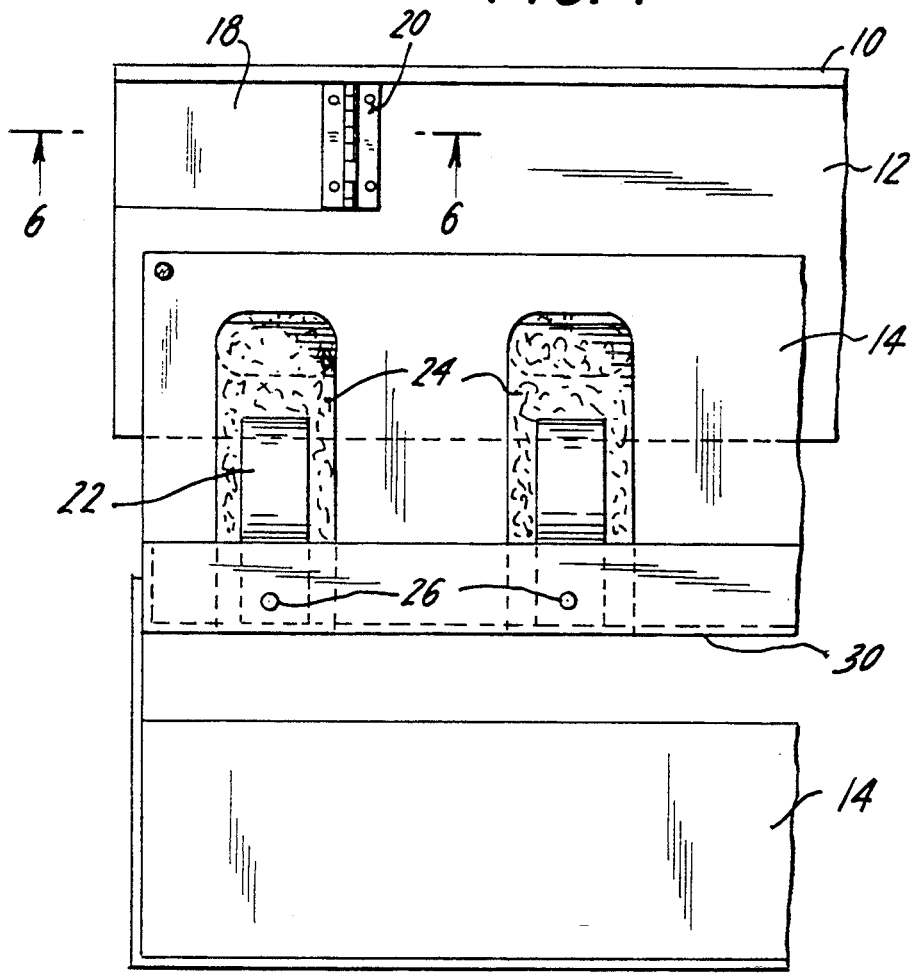
FIG. 4
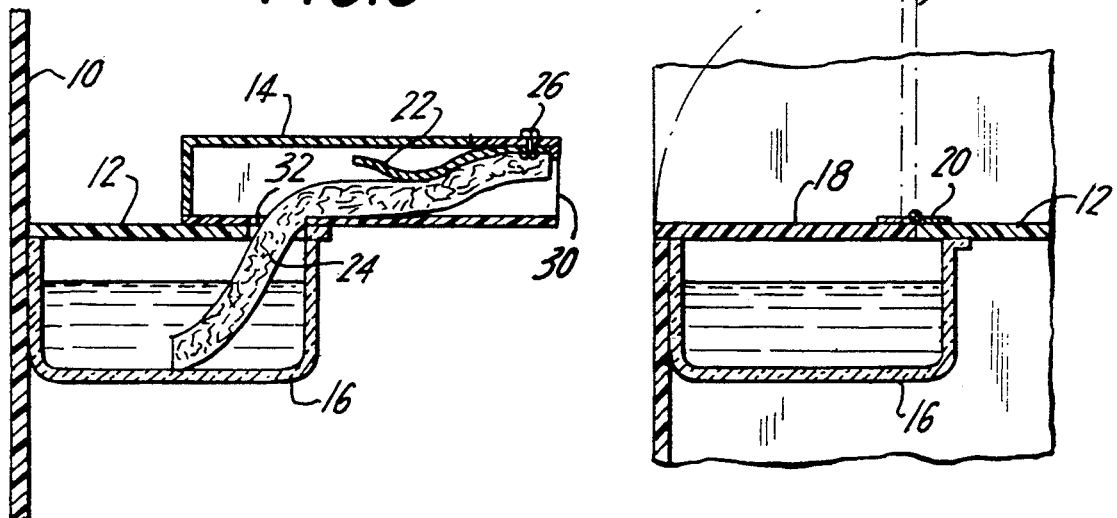
FIG. 5
FIG. 6

DISINFECTION RACK

BACKGROUND OF THE INVENTION

1. Field of the Invention

The field of the invention relates to disinfection rack whose function is to protect and disinfect the superior surface of vials in addition to being a mountable holder for these same vials.

2. Brief Description of Prior Art

The use of multiple-dose vials in medicine has proven to be a cost efficient way for a health professional to administer injectable medications to patients. Besides cost, there are other advantages these multiple-dose vials have over ampules and prefilled syringes. For example, allowing the physician to fill the syringe with the exact dose desired, and mixing a number of compatible medications in a single syringe to be given in one injection are two such advantages. Typically the person who is to administer the medication must go through a number of steps to fill a syringe from a multiple-dose vial. Usually these steps include locating the appropriate medication in a cabinet drawer among a group of vials, then place it on a counter top, find an alcohol soaked gauze, clean the top of the vial, and then proceed to draw up the medication into the syringe. This cleaning is necessary because once the vial top has been removed, a nonremovable rubber stopper is now exposed. To remove the medication from the vial one must pierce the rubber stopper with a sterile needle which may become contaminated if the top of the vial is not cleaned properly.

The present invention provides a device to mount, display, store, organize, and disinfect a plurality of vials. A number of racks for storage of objects have be disclosed such as those in U.S. Pat. No. 4,687,108 (1987), Kermodle; where a flange item holder is used to mount various object by their base and U.S. Pat. No. 4,925,630 (1990) Grunwald, which holds sample vials by their base. Other prior art such as racks described in U.S. Pat. Nos. 4,482,065 (1984) Altemose; and 4,887,726 (1989) Clanire; are large bottle holders like those used for wine, or as in U.S. Pat. No. 4,325,486 (1982) Neal, an overhead rack for glass stemware. While all above mentioned letters are suitable for there intended purpose they do not disinfect the objects they hold. Some disinfecting devices such as those disclosed in U.S. Pat. Nos. 4,863,698 (1989) Ryder et al, are used for sterilizing glass vials with an object inside,(ie. Contact lenses) by using heat, or 5,106,595 (1992) Ellenberg, sterilizes the mouth of containers by applying a disinfectant with atomizers. These inventions are novel for their intended purpose but do fail to provide a rack or system for mounting vials, and many disinfection systems use heat which will alter the chemical structure of the medication if it is subjected to extremes in temperature or radiation.

OBJECTIVES AND ADVANTAGES

It appears that the disinfection rack disclosed has the ability to fulfill the needs of mounting, organizing, and displaying vials, while disinfecting the superior surface of the vial when not in use. Also this device will physically clean the top of the vial during its removal and insertion into the rack and disinfection is accomplished through cold sterilization.

A principal objective of the invention is to provide a clean or sterile environment for multiple-dose vials.

Another objective is to provide a place of storage for a number of vials.

Still another objective is to allow the user to read the label on the outside of the vial making it readily identifiable as in an emergency situation.

Another objective is to accommodate different vial sizes within the same disinfection rack.

Another objective is to prevent accidental contamination of a vial during storage in a drawer or cabinet.

Still another objective is to use a disinfection fluid at room temperature as to not expose the vial to heat or radiation.

A further objective is to allow for the organization of medication or other materials contained in the vials.

Yet another objective is to physically clean the top of the vial during its insertion and removal from the invention.

BRIEF DESCRIPTION OF DRAWINGS

These objectives along with the inventions' operation will become apparent with the following descriptions and clarified with referral to the drawing provided.

FIG. 4 is a top view of the invention with components exposed.

FIG. 5 is a vertical section through the device taken along the line 5—5 of FIG. 1.

FIG. 6 is a vertical section through the disinfection rack taken along the line 6—6 of FIG. 4.

Figure 1:
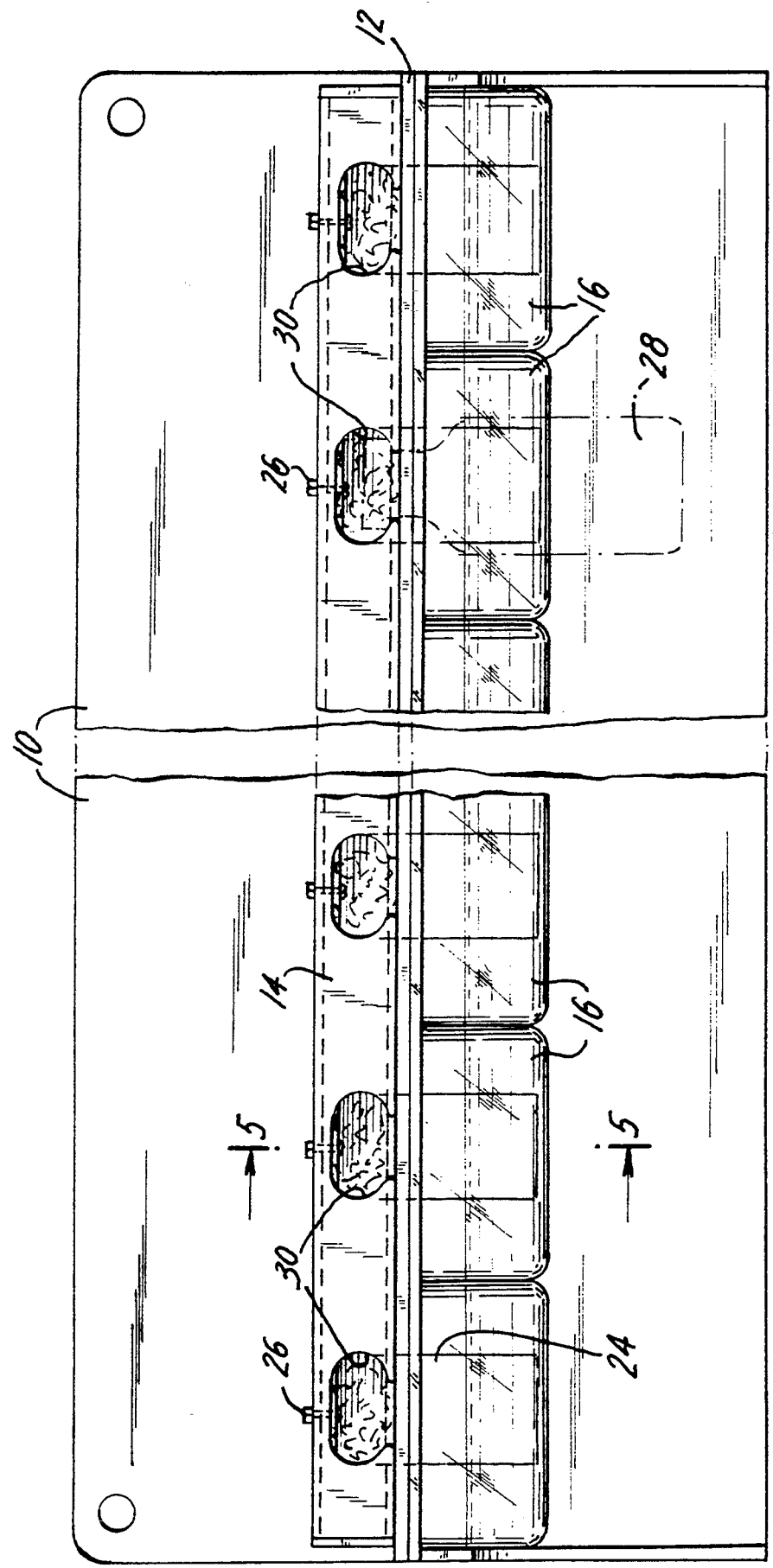
FIG. 1 is a view of the device as seem looking directly at the face or front surface.

| Reference Numerals In Drawings | | | |
|---|---|---|---|
| 10 | mounting plate | 12 | reservoir cover |
| 14 | disinfection chamber | 16 | fluid reservoir |
| 18 | door | 20 | door hinge |
| 22 | spring | 24 | wick |
| 26 | screw | 28 | multiple-dose vial |
| 30 | opening to disinfection cell | 32 | opening to reservoir |

DESCRIPTION OF EMBODIMENT—FIG. 1 TO 6

Referring to FIG. 1, the disinfection rack is centered around a reservoir 16 which is preferably made of a thin, durable, light weight substance such as clear plastic or other such material, which serves as the foundation of the invention and its' related parts. Reservoir 16 has the capacity to hold sterilizing or disinfecting fluid (ie alcohol, glutaraldehyde etc.). To reservoir 16 a mounting plate 10 provides the invention with a means to secure it to a wall, cabinet door, or other object. On top of reservoir 16, a reservoir cover 12 serves as both lid to protect disinfecting fluid within reservoir 16, and a mounting plate for a disinfection chamber 14 on its dorsal surface.

Continuing with FIG. 1 disinfection chamber 14 has a number of cell openings 30 on its side surface which faces outward. Each cell opening 30 is shaped to accommodate the top and neck of a typical multiple-dose medication vial 28.

Figure 2:
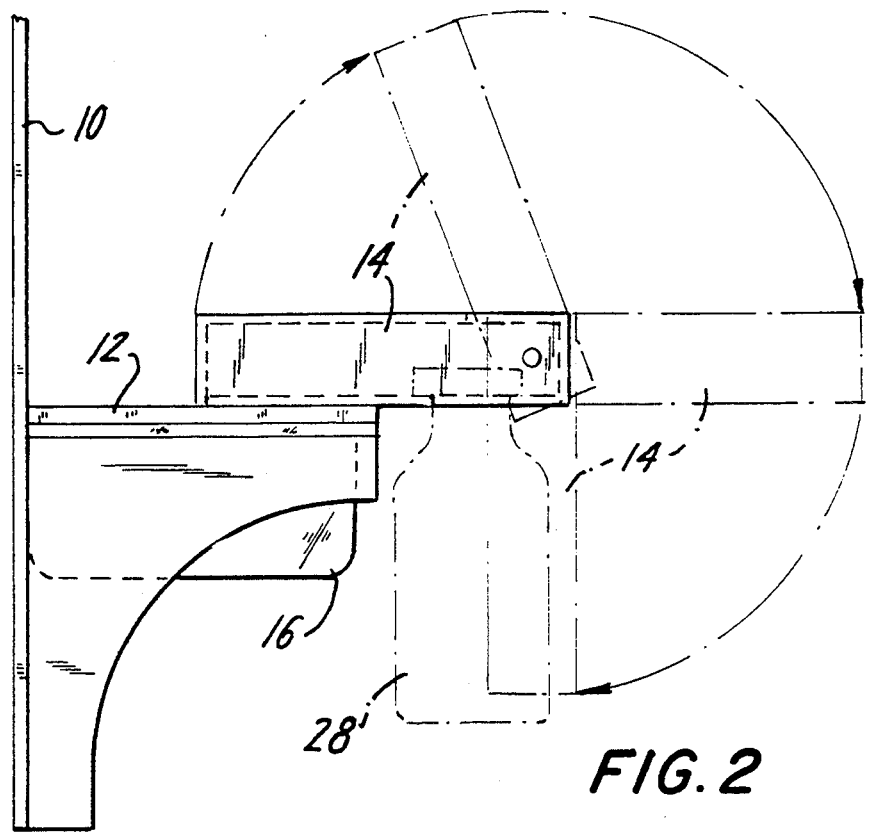
FIG. 2 is a view of the side or lateral aspect of the device.

Directing ones attention to FIG. 2, a side or lateral view of disinfection rack is shown with multiple-dose vial 28 suspended by the neck of vial 28. To accomplish this multiple-dose vial 28 rests on the bottom plate of disinfection chamber 14 which extends a distance away from reservoir 16. This arrangement allows multiple-dose vials of different heights and sizes to be accommodated by the device. Disinfection chamber 14 dorsal surface can be opened as pictured and is discussed below. (see FIG. 4).

Figure 3:
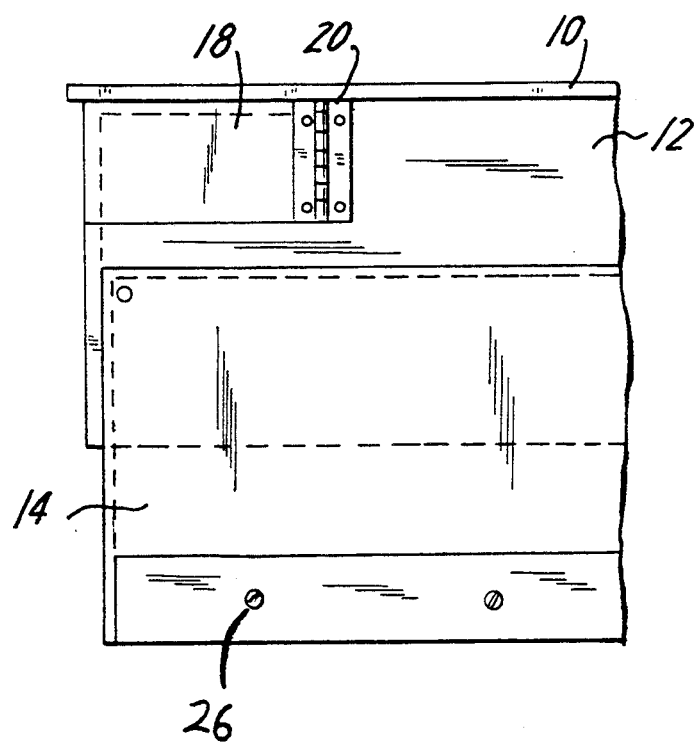
FIG. 3 is a top view of the invention.

Directing attention to FIG. 3 a dorsal view of the disinfection rack. Reservoir cover 12 has an opening, door 18 which is connected by hinge 20 whose purpose when open enables reservoir 16 to be filled with disinfection fluid. FIG. 3 also shows disinfection chamber 14 depicted with its top in the closed position.

FIG. 4 illustrates a dorsal view of disinfection rack with top of disinfection chamber 14 in an open position. This allows exposure of a spring 22 and a wick 24 which are connected to disinfection chamber 14 by screw 26. The function and operation of spring 22 and wick 24 are explained in detail under description of FIG 5 and in the Operation section below.

FIG. 5 is a vertical section of disinfection rack taken along the line 5—5 of FIG. 1. Note spring 26 and wick 24 are attached to dorsal surface of disinfection chamber 14 by screw 26. Nick 24 passes through an opening 32 in bottom plate of disinfection chamber 14 and reservoir cover 12 into fluid reservoir 16.

FIG. 6 is a vertical section through the disinfection rack taken along the line 6—6 of FIG. 4 and shows the relationship of door 18 to fluid reservoir 16. When door 18 which is attached to reservoir it cover 12 by hinge 20 is open, disinfection fluid may be added to fluid reservoir 16 directly.

Operation—FIGS. 1, 2, 4, 5, 6

Disinfection Tack is simple to operate. First one must fill fluid reservoir 16 with an antibacterial liquid such as alcohol or glutaraldehyde by opening door 18. Once fluid reservoir 16 is filled door 18 is closed. The antibacterial solution is absorbed by wick 24 and travels along its entire length to its distal end terminating at screw 26 within disinfection chamber 14 and saturates entire wick 24.

Insertion of Vial: Vial 28 is inserted through opening 30 in disinfection chamber 14 and slides along the bottom surface of disinfection chamber 14. During insertion the dorsal aspect of vial 28 comes in contact with wick 24 which is saturated with a solution (ie. alcohol). As one continues to slide vial 28 deeper into disinfection chamber 14, spring 22 applies increased tension to the superior surface of vial 28. Spring 22 keeps wick 24 in contact with the top vial 28 as long as vial 28 is in disinfection chamber 14. In addition spring 22 also causes wick 24 to physically scrub the top of vial 28 while being inserted into disinfection chamber 14.

Removal of vial: When a person removes vial 28 from disinfection chamber 14, a second physical scrubbing of the top of vial 28 occurs. As vial 28 slides along the bottom of disinfection chamber 14, wick 24 saturated with alcohol remains in contact with vial 28 until opening 30 of the disinfection chamber 14 is reached and vial 28 exits.

Vial 28 dorsal surface is clean and needle may be inserted at this time to remove the contents of vial 28 without feat of contamination.

Summary and Scope

After reading the forestated description of the disinfection rack, it becomes apparent that this invention will provide its operator a simple way to store and display a number of vials. It will also help organize the materials contained in the vials within a rack. The disinfection rack will keep the top of the vials in a sterile environment without the use of heat or radiation. This novel device also allows visual access to the amount of medication left in a vial, and enable one to choose the correct medication by reading the label without having to remove or pick up a vial. This is important in an emergency situation where time and confusion should be kept at a minimum. Furthermore the disinfection rack may be mounted to any wall, cabinet, within refrigerators, and emergency vehicles. Also the disinfection rack:

does not require special antimicrobial agents, most liquids will travel along its wick 28;

permits immediate use in an emergency situation;

handles multiple-dose vials whether large or small within the same rack;

requires no electric or thermal energy;

it vastly improves on present storage of vials, (ie. in drawers and cabinets) and reduces risk of contamination;

it has application in hospitals, (ie. emergency rooms, clinics, nurses stations, medication rooms, and on the medication carts); and, it can be used in laboratories, doctors offices, veterinarian offices, and pharmacies; and, disinfection rack can be mounted in ambulances, and emergency vehicles.

The above description shall not be construed as limiting in ways in which this invention may be practiced but shall be inclusive of many other variation by those skilled in the art who's changes or modification could be made without departing from the broad interests, intent, and true spirit of this invention.

Having described my invention what is claimed is:

1. A disinfection rack for organizing, displaying, and sterilizing vials comprising:

a disinfection chamber having a plurality of slots, each of which are shaped to accommodate the top and neck of a vial, and having an opening on a bottom surface for receiving a first end of a wick, a reservoir containing sterilization fluid and having an opening on a superior surface for receiving a second end of a wick, a portion of which reservoir superior surface is attached to a bottom surface portion of the disinfection chamber, a wick engaging a surface of a top of a vial within the disinfection chamber and said sterilization fluid travelling from said reservoir through said wick and to said vial top surface, and means for providing pressure to hold said wick against said vial top surface during sterilization.

* * * * *